United States Patent
Hermey et al.

(10) Patent No.: US 12,095,242 B2
(45) Date of Patent: Sep. 17, 2024

(54) GUIDE APPARATUS FOR A CABLE GUIDE DEVICE COMPRISING A CABLE GUIDE DEVICE

(71) Applicant: IGUS GMBH, Cologne (DE)

(72) Inventors: Andreas Hermey, Hennef (DE); Karl Oskar Lapiere, Troisdorf (DE)

(73) Assignee: IGUS GMBH, Cologne (DE)

( * ) Notice: Subject to any disclaimer, the term of this patent is extended or adjusted under 35 U.S.C. 154(b) by 182 days.

(21) Appl. No.: 17/753,687

(22) PCT Filed: Sep. 9, 2020

(86) PCT No.: PCT/EP2020/075232
§ 371 (c)(1),
(2) Date: Mar. 11, 2022

(87) PCT Pub. No.: WO2021/048228
PCT Pub. Date: Mar. 18, 2021

(65) Prior Publication Data
US 2022/0344924 A1    Oct. 27, 2022

(30) Foreign Application Priority Data

Sep. 11, 2019   (DE) .................. 20 2019 105 021.7

(51) Int. Cl.
*H02G 11/00*    (2006.01)
*A61B 6/00*    (2006.01)

(52) U.S. Cl.
CPC .......... *H02G 11/003* (2013.01); *A61B 6/4441* (2013.01)

(58) Field of Classification Search
CPC ........................ H02G 11/003; A61B 6/4441
See application file for complete search history.

(56) References Cited

U.S. PATENT DOCUMENTS 6,250,443 B1 *  6/2001  Richter .................. H02G 11/02
                                                           191/12.2 R
8,662,748 B2     3/2014  Herrmann et al.

FOREIGN PATENT DOCUMENTS

DE         19743317        2/1999
DE       102010020780     11/2011
(Continued)

OTHER PUBLICATIONS

International Search Report from corresponding PCT Appln. No. PCT/EP2020/075232, dated Nov. 19, 2020.
(Continued)

*Primary Examiner* — Hugh Maupin
(74) *Attorney, Agent, or Firm* — Grossman, Tucker, Perreault & Pfleger, PLLC (57) ABSTRACT

A guide apparatus for a line guide device comprising at least one such device, wherein the line guide device has a free internal cross-section for receiving at least one line and a plurality of successively arranged portions which are spatially deflectable relative to each other and it can be disposed in an arrangement comprising a lower run, an upper run and a deflection region connecting same and having a deflection axis, wherein the guide apparatus is formed at least with a longitudinal portion thereof or over the entire length thereof, with which it guides the line guide device in the longitudinal direction thereof, with a C-shaped guide region having a curvature axis of the C-arc and having a concave arc inner curvature and a convex arc outer curvature. The guide apparatus has a deflection device having a deflection axis, wherein the deflection region of the line guide device is guided around the deflection device, and the axis of the deflection device includes an angle with the curvature axis of the C-shaped guide region of the guide apparatus, wherein one of the side boundaries of the line guide device is
(Continued)

arranged facing towards the convexly curved outside of the C-shaped guide region of the guide apparatus.

19 Claims, 5 Drawing Sheets

(56)  References Cited

FOREIGN PATENT DOCUMENTS

| | | |
|---|---|---|
| DE | 102015205046 | 9/2016 |
| DE | 202018004739 | 10/2018 |
| EP | 3527138 | 8/2019 |
| JP | 3022363 | 3/2000 |
| JP | 2001061825 | 3/2001 |

OTHER PUBLICATIONS

Written Opinion from corresponding PCT Appln. No. PCT/EP2020/075232, dated Nov. 19, 2020.
Office Action from related Japanese Appln. No. 2022-516093, dated May 7, 2024. English translation attached.

* cited by examiner

GUIDE APPARATUS FOR A CABLE GUIDE DEVICE COMPRISING A CABLE GUIDE DEVICE

FIELD

The invention concerns a guide apparatus for a line guide device.

BACKGROUND

The guide apparatus of the general kind set forth has a C-shaped guide region for guiding the line guide device so that the line guide device is also arranged on the guide apparatus in the form of a C-shaped arc in the longitudinal direction of the line guide device. Such guide apparatuses are used for example in C-arm X-ray systems or other medical diagnostic equipment. Generally, arranged at the opposite end regions of the C-shaped arcuate guide region of the guide apparatus or a prolongation thereof are a signalling device like an X-ray emitter on the one hand and a signal-receiving device like for example a detector, for example also in the form of an image amplifier or imaging system, or corresponding other consumers for media transmitted by the lines. In that case the guide apparatus is generally arranged on a holder of the machine or item of equipment including same, wherein the holder is arranged for example at the curvature outside of the C-shaped guide region of the guide apparatus. In that case the guide apparatus is generally displaceable in its longitudinal direction with respect to the holder, wherein the holder generally locally engages in relation to the longitudinal extent of the guide apparatus and therefore extends only over a relatively short part of the longitudinal extent of the guide apparatus. Upon displacement of the guide apparatus it therefore describes an envelope curve in relation to the curvature axis of the C-shaped guide region, accordingly when the guide region is in the form of a circular arc-shaped portion it travels around a cylindrical surface in the peripheral direction thereof. In that way an object arranged at the centre of the C-shaped guide region like for example a patient can be investigated from a plurality of directions without a change in position. These descriptive statements relating to a guide apparatus of the general kind set forth and/or the item of equipment or machine can moreover also be implemented in relation to the subject-matter of the invention insofar as they do not contradict the description thereof.

There is now a need to enlarge the extent of the C-shaped guide region of the guide apparatus so that it therefore extends over a greater angular extent or rotary angle about the axis of curvature of the arc and/or to be able to move the C-shaped guide region over a greater angular region around the axis of curvature, that is to say over a greater distance in the longitudinal extent of the C-shaped guide region, in particular in the direction towards the installation surface of the machine or item of equipment including the guide apparatus. In the case of apparatuses of the general kind set forth however that gives rise to various problems. On the one hand, in previously known guide apparatuses in which the line guide device is arranged in cantilever relationship and the upper and lower runs of the line guide device are arranged one above the other in relation to the direction of the force of gravity and at a spacing relative to each other the cantilever length becomes too great if the extent of the C-shaped guide region is increased. The result of this is that the upper and lower runs come region-wise into contact with each other, which considerably adversely affects the smoothness of operation of the line guide device and can lead to increased abrasive wear. On the other hand the deflected line guide device, in which the upper and lower runs are arranged concentrically in relation to the axis of curvature of the C-shaped guide region of the line guide device, takes up a considerable amount of structural height. That however often restricts displacement of the guide apparatus relative to the installation surface of the machine or item of equipment including the guide apparatus, and that in turn limits the range of application of the machine or item of equipment.

SUMMARY

The object of the invention is to improve a guide apparatus of the general kind set forth or a machine or item of equipment having same, in such a way that the C-shaped guide region of the guide apparatus is displaceable over a greater rotary angle about the axis of curvature thereof, possibly even in restricted space conditions in relation to the ground clearance of a machine or item of equipment including the guide apparatus, and a high level of operating smoothness is afforded even in the case of a greater longitudinal extent of the line guide device.

According to the invention the guide apparatus has a deflection device with a deflection axis which is arranged at the deflection region of the line guide device and about which the deflection region of the line guide device is guided. In that case the deflection device is preferably coupled at the inside at the deflection region. In that way the deflection device is arranged in the deflection region of the line guide device in various or preferably all displacement positions of the line guide device and the line guide device is deflected around the deflection device, that is to say it is guided in a condition of bearing against same in the deflection region. In addition the deflection device is so arranged that the axis thereof includes an angle with the curvature axis of the C-shaped arcuate guide region of the guide apparatus, that is to say an angle that is not equal to 0°, therefore inclinedly or preferably transversely to same. In addition the line guide device is so arranged that one of the lateral boundaries thereof faces towards the convexly curved curvature outside of the C-shaped arcuate guide region. In that case the side boundary of the line guide device represents a preferably continuous side boundary of the upper and lower runs as well as the deflection region of the line guide device and thus extends transversely or in particular perpendicularly to the mutually facing surfaces of the upper and lower runs. In that arrangement the guide apparatus determines the position of the line guide device in relation to the longitudinal orientation thereof by guidance thereof. The line guide device is guided in the shape of a C-shaped circular arc in relation to the longitudinal extent of the line guide device by the C-arc of the guide apparatus.

The structure according to the invention provides a particularly small structural height in respect of the line guide device or of same together with the guide apparatus as the line guide device with upper and lower runs is so-to-speak "laid on the side" in relation to the guide region of the C-shaped arc of the guide apparatus—in contrast to a conventional arrangement—as the line guide device is arranged with one of the side boundaries facing towards the C-shaped arc of the guide apparatus. The structural height here is therefore the structural height in a radial direction relative to the curvature axis of the C-shaped arc. In that way the guide apparatus can be displaced further in a direction towards the installation surface of the machine or item of equipment or displacement is not impeded by that surface.

In that case the installation surface is generally the floor of a premises, that is to say a room in a building.

In addition the arrangement of the deflection device in the deflection region of the line guide device which thus even in different displacement positions of the line guide device is preferably always arranged in the deflection region and the line guide device is guided in a condition of bearing against the deflection device around same gives a comparatively close and stable guidance effect for the line guide device which thus in particular prevents the upper and lower runs of the line guide device from coming into contact with each other whereby they could interfere with smooth running upon displacement of the line guide device even in the case of long peripheral extents of the C-shaped arc of the guide apparatus or in the case of great lengths of the line guide device.

Generally in the context of the invention the guide region in the shape of a C-arc of the guide apparatus will be abbreviated as "C-arc of the guide apparatus" or "C-arc". Generally in the context of the invention the term "deflection region" is used to denote a deflection region of the line guide device.

The curvature axis of the C-arc thus corresponds to the rotation axis of the C-arc. The curvature axis is thus at the centre of the C-arc. In the case of a C-arc which is in the shape of a circular arc the curvature or rotation axis therefore corresponds to the entre point axis of the C-arc, which is therefore arranged at the centre point of the C-arc and perpendicularly to the main axis of the C-arc.

The line guide device can be for example in the form of a link chain as is used in relation to energy guide chains in which a multiplicity of individual chain links are hingedly connected together and adjacent links are pivotable relative to each other about a pivot axis, wherein spatial deflection is afforded by such pivotal movement. Such chain links generally comprise two laterally mutually spaced side portions and an upper bar and a lower bar which together define the internal cross-section of the line guide device. The side portions and transverse bars can be respectively in the form of individual components or can be integrally connected together, for example by forming a U-shaped part including a transverse bar and two side portions formed thereon or the like. In that case the chain links are preferably pivotable about a hinge axis provided by the hinge elements thereof, without however being restricted thereto. By way of example the individual chain links of a line guide device can also be hingedly connected together by hinge connections in the manner of a ball joint or in some other fashion. The line guide device can be for example in the form of or in the manner of an articulated tube having a multiplicity of hingedly interconnected tube portions. The line guide device however generally can also be of a one-piece structure or include a plurality of longitudinal portions which each have a plurality of mutually laterally spaced pairs of side plates or side boundaries of the internal cross-section and thus also the line guide device itself. Thus for example the arrangement may provide U-shaped chain links with an openable or subdivided transverse bar which is releasably fixed to a band extending over the entire length of the line guide device or is formed integrally thereon. Said endless band can additionally perform the function of transverse bars and delimit the internal cross-section or receiving space of the line guide device, wherein the side parts of portions of the line guide device can also be formed directly on the endless band. The line guide device can for example also be in the form of a deformable tube or hose, for example also a slit tube or hose, wherein the slits or corresponding other material openings or material weakenings provide the desired flexibility or bendability of the line guide device, in which case spatial deflectability of adjacent portions of the line guide device is afforded by the flexibility or bendability. The "deflectability" of the portions of the line guide device is thus generally not restricted in the context of the invention to the provision of specific defined pivotal hinge regions between said portions. Spatial deflectability is thus generally afforded in accordance with the invention in each case perpendicularly and/or transversely to the longitudinal direction of the line guide device, wherein "perpendicular" here is used to denote in the direction of the upper run towards the lower run or viceversa. The adjacent portions of the line guide device, that are spatially deflectable relative to each other, are thus generally preferably spatially deflectable relative to each other about at least two directions which are at an angle relative to each other, the directions preferably being perpendicular to each other.

The line guide device can be for example of a circular cross-section, that is to say for example it can be in the shape of a tube of circular cross-section, or a rectangular cross-section, without being restricted thereto.

The guide apparatus according to the invention is particularly preferred if the curvature axis of the C-arc of the guide apparatus is arranged at an angle of 30°-150°, preferably 45°-135° or in particular 60°-120°, particularly preferably about 90°, to the direction of the force of gravity. The direction of the force of gravity is usually at the same time the Z-direction of an installation room or area for the machine or item of equipment including the guide apparatus. The advantages according to the invention are then particularly valuable.

Preferably the axis of the deflection device, in particular in the form of a deflection roller, and thus also the deflection axis of the deflection region of the line guide device is arranged at an angle of 30°-150° or 45°-135°, preferably at an angle of 60°-120°, particularly preferably at an angle of about 90° to the curvature axis of the C-arc of the guide apparatus. That provides a stable spatial position of the line guide device with the arrangement thereof at the C-arc of the guide apparatus, wherein the line guide device is "laid on the side" relative to the guide surface of the C-arc. Upon displacement of the line guide device this therefore prevents the upper run of the line guide device from coming into contact with the lower run thereof. In addition that provides a comparatively small structural height for the line guide device and thus also the guide apparatus including same. That is also the case in particular when the curvature axis of the C-arc is at an angle relative to the direction of the force of gravity or the Z-axis of the installation area of the machine or item of equipment including the guide apparatus, in particular when the curvature axis of the C-arc is arranged transversely or preferably at 90° relative to the force of gravity.

Preferably the C-shaped guide region of the guide apparatus extends over >50% or >75%, preferably over >85% of the longitudinal extent of the line guide device, further preferably over the total longitudinal extent of the line guide device. The term "total longitudinal extent" of the line guide device is used to denote the length thereof in a displacement state or arrangement of the line guide device with the maximum spacing of the two opposite ends thereof relative to each other, that is to say when for example the two connecting devices at the two opposite ends of the line guide device are at maximum spacing from each other. In that way the line guide device can be adapted over its total length to the configuration of the C-arc of the guide apparatus and in that case is preferably also guided in a C-arc over the specified longitudinal extent by the guide apparatus.

That provides that arcuate displacement of the guide apparatus and thus also the consumer arranged thereon, which is supplied by the line in the line guide device, is particularly easily possible. Optionally, for example for other situations of use, the C-arc of the guide apparatus can also extend only over a part of the total longitudinal extent of the line guide device, for example through greater than or equal to 30% or greater than or equal to 50%, in particular greater than 75% or greater or equal to 85%.

Preferably the C-shaped guide region of the guide apparatus extends over >90° or >120° or up to 180° or more.

The C-shaped arcuate guide region of the guide apparatus preferably extends in respect of height over at least a part of the upper run and at least a part of the lower run, preferably over the entire heightwise extent of the upper run and/or the entire heightwise extent of the lower run. The "height" of the upper and lower runs is established in that case by the direction in which the upper and lower runs are arranged in mutually superposed relationship or are mutually spaced in height. That can provide for good and effective guidance of the line guide device by the C-arc of the guide apparatus and both the upper run and also the lower run of the line guide device can be guided laterally, that is to say transversely or perpendicularly to the longitudinal extent of the line guide device, by the C-arc.

Preferably the C-shaped guide region of the guide apparatus is in the form of a rail, representing a structurally simple configuration which at the same time is mechanically stable. The rail preferably extends over the height of the line guide device so that the upper and lower runs thereof can bear laterally against same. The rail in that case can be of a multi-part configuration or however can also be in one piece. The line guide device guided by the guide apparatus can in that case bear laterally against the rail.

The respective end region of the line guide device is generally connected in accordance with the invention to the respective connecting device, preferably in such a way as to carry a tensile force. The connecting device can respectively include a strain relief means for the line or lines guided in the line guide device. One of the connecting devices is preferably fixed to an entrainment member of the line guide device or is moveable together with such or is part of such an entrainment member, wherein the end of the line guide device connected to the entrainment member is displaced by movement of the latter. One or other of the connecting devices preferably constitutes a fixed point with respect to the line guide device and is preferably fixed to a holder of the machine or item of equipment for the guide apparatus or is connected thereto so as to carry a tensile force. The respective fixing is preferably implemented in such a way that the parts which are fixed together are not variable in position relative to each other. The run of the line guide device which is arranged at or fixed to the moveable connecting element is referred to in the context of the invention as the "upper run" and the other run of the line guide device is referred to as the "lower run".

Preferably the C-shaped guide region of the guide apparatus extends over at least 50% or particularly preferably >75% or >90% or 100% of the longitudinal extent of the line guide device in the displacement state thereof at the maximum spacing of the two end regions of the line guide device from each other. In that way the C-arc is displaceable through an angular range which is of the maximum size about the curvature axis of the C-arc. In that way the range of application of corresponding machines or items of equipment is enlarged as for example the line guide device can be held very exactly in an arcuate position defined by the C-arc of the guide apparatus without the upper run and the lower run of the line guide device coming undesirably into contact with each other upon displacement. The line guide device in that case preferably bears against the C-shaped guide region of the guide apparatus over >25% or >50% of the total length thereof, particularly preferably >75% or >90% or practically 100% of the total length thereof. The line guide device can bear with said region loosely or however also with a certain amount of force, in relation to the available region.

Generally in accordance with the invention the line guide device can be guided around the deflection device in a condition of bearing loosely against same. The line guide device can also be guided about the deflection device with the application of force in respect of the deflection device against the deflection region of the line guide device in its longitudinal direction, thereby affording a further improved guidance effect for the line guide device while further reducing sag of portions thereof as the line guide device is so-to-speak tensioned by the deflection device in the longitudinal direction thereof. The deflection device can possibly bear with a constant force against the deflection region of the line guide device.

Generally in accordance with the invention the deflection device, at least during some or predetermined displacement positions of the line guide device, for example over >50% or >75% of the displacement travel of the line guide device, or particularly preferably permanently throughout the entire displacement movement of the line guide device in the longitudinal direction of the extent of the line guide device, is bearing against the deflection region of the line guide device, preferably loosely or optionally under the effect of a force. The deflection device is thus preferably permanently positioned during displacement of the line guide device by means of said device for changing the position of the deflection roller in the deflection region of the line guide device so that the line guide device is guided around the deflection device in a state of bearing against same. Upon displacement of the line guide device the deflection region thereof is stabilised thereby. In particular however in that way the line guide device can be tensioned, during some or predetermined displacement positions of the line guide device or particularly preferably permanently throughout the entire displacement movement of the line guide device, in the longitudinal direction and preferably at the same time is subjected to a force laterally against the C-arc of the guide apparatus, whereby the position of the line guide device is particularly exactly defined and for example sagging of portions thereof is effectively prevented. A certain tensioning is already afforded if any longitudinal play in the line guide device is removed or eliminated by the tensioning, in which case such a longitudinal play, for example because of play in the joint connections between adjacent portions of the line guide device, like for example in the case of a link chain, or elastic stretching of joint regions of the device, can occur. Preferably the force applied is such that the line guide device is play-free in the longitudinal direction thereof by virtue of that force.

Preferably a deflection device is provided at every deflection region of a line guide device, even if there are provided a plurality of line guide devices.

According to a preferred embodiment generally in accordance with the invention the deflection device is in the form of a deflection roller about which the line guide is deflected. In that case the deflection roller is preferably rotatable freely about the axis of rotation (also referred to as the "spindle") thereof. A plurality of deflection rollers can also be provided in an arcuate arrangement on a holder. Other deflection devices however are also conceivable, for example the line guide device can be moved slidingly over a deflection part. If there are provided a plurality of line guide devices on the guide apparatus then preferably the deflection device for each of those line guide devices is in the form of a deflection roller. A configuration in the form of a deflection roller is structurally simple, permits an exact line guide device and possibly also provides a low-wear embodiment when force is applied in respect of the deflection device at the deflection region of the line guide device in the longitudinal direction thereof.

Preferably there is provided a device for changing the position of the deflection device in the longitudinal direction of the line guide device, which positions the deflection device upon displacement of the line guide device in the longitudinal direction thereof at the deflection region, that is to say holds the deflection device in its position at the deflection region of the line guide device independently of the displacement position of the line guide device. In that case the deflection device can bear loosely against the deflection region or can be subjected to a force in the longitudinal direction of the line guide device with respect to the deflection region. The said device is preferably so designed that, at least during some or predetermined displacement positions of the line guide device or particularly preferably permanently throughout the entire displacement movement of the line guide device, in the longitudinal direction of the extent of the latter, the deflection device bears against the deflection region of the line guide device, possibly under the action of a force. By virtue of the applied force the line guide device has a certain degree of prestressing so that the spatial arrangement thereof is even better defined by the guide apparatus, in particular also by interaction with the deflection device, and unwanted sagging of portions of the line guide device is prevented to an increased extent. That ensures that upon displacement of the line guide device portions of the line guide device do not come into contact in an unwanted fashion with other portions of the guide apparatus, including other portions of the line guide device, or sag down, which could adversely affect smooth operation of the line guide device or could increase wear.

Preferably the deflection device is variable in position upon displacement of the line guide device, more specifically in the longitudinal direction of the C-shaped guide region of the guide apparatus, whereby the deflection region of the line guide device and the spatial arrangement thereof overall can be stabilised. Upon displacement of the guide apparatus preferably the deflection device is displaced in the longitudinal direction of the C-shaped guide region of the guide apparatus relative to the guide apparatus.

According to a preferred embodiment the deflection device is forcibly displaceable with the line guide device and therefore upon displacement of the line guide device by virtue of a given coupling to the line guide device is displaced together with same without further devices for varying the position of the deflection device being required.

Alternatively preferably the device for positioning at the deflection region, possibly also for applying force in respect of the deflection device in the longitudinal direction of the line guide device against the deflection region, can be in the form of a device operated by actuator means, wherein the actuator can be actuated for example by a resilient action, by electric motor means, hydraulically or pneumatically. The actuator is different from the line guide device. The deflection device can be subjected to a force against the deflection region by actuation of the actuator. In that way the position of the deflection device can be set in self-adjusting mode. The actuator can be mounted to the guide apparatus, for example the C-arc thereof, possibly with the formation of a supporting abutment for positioning or for applying force. The deflection device can also be of such a configuration that it is positioned by the displacement movement of the line guide device at the deflection region thereof, for that purpose for example it can be coupled at the line guide device for changing position with same, so that an additional actuator can be unnecessary.

Preferably the regions of the guide device, in particular the C-arc thereof, which come or could come into contact with the line guide device upon displacement thereof, are equipped with a sliding friction-reducing surface in order to reduce the sliding friction resistance if the line guide device comes into contact with the guide regions of the guide apparatus.

Preferably the deflection device is mounted freely rotatably about its longitudinal axis by means of a bearing. The bearing can be held longitudinally displaceably to the C-shaped guide region of the guide apparatus. That provides a structurally simple configuration, wherein by the change in position of the deflection device, this ensures that it is always in the deflection region of the line guide device upon displacement thereof. That also ensures in a simple manner that, upon longitudinal displacement of the deflection roller bearing, the line guide device can bear laterally against the C-arc. In addition that construction is particularly advantageous in terms of the structural configuration and minimisation of wear upon displacement of the guide apparatus.

The deflection device preferably projects above the line guide device at least over a part of the height thereof and therefore extends over at least a part of the height of the upper run and/or a part of the height of the lower run. The "height" of the upper and lower run is respectively the extent thereof in the direction towards the opposite run, from the upper and lower run respectively. The projecting region of the deflection device in relation to the line guide device means that the line guide device is stabilised in its position at the deflection device, in the transverse direction of the line guide device, that is to say in the direction towards or away from the guide apparatus, and is secured to prevent unintended spacing from the deflection device, that is to say for example to secure it against lateral downward slippage from the deflection device. The deflection device therefore particularly preferably projects in height at least partially over the upper and/or lower run on the side of the line guide device, that is opposite to the C-shaped guide region of the guide apparatus, preferably by >10% or >20%, particularly preferably >30% or 50% or more in respect of the height of the upper and/or lower run. Additionally or possibly alternatively the deflection device preferably projects on the side of the line guide device, that is towards the C-shaped guide region of the guide apparatus, in respect of height at least partially beyond the upper and/or lower run, preferably by >10% or >20%, particularly preferably >30% or 50% or more in respect of the height of the upper and/or lower run, whereby the line guide device is spaced in the deflection region from the guide apparatus, whereby the running properties thereof are improved.

Preferably there is provided a support device for the upper and/or lower run of the line guide device, which supports the upper and/or lower run outside the deflection region of the respective run in the direction towards the respective other run, which leads to a more uniform displacement of the line guide device in the longitudinal direction thereof. The region of the support device, that supports the respective run, is thus preferably disposed between the upper and lower run respectively. Alternatively or additionally the support device can be arranged at the top side of the upper run and/or the underside of the lower run. A plurality of support devices can be arranged distributed over the length of the line guide device. A given support device can preferably bear both against the upper run and also the lower run. The running properties of the line guide device are in particular also improved by the support device if the curvature or rotational axis of the arcuate guide apparatus is not arranged perpendicularly to the direction of the force of gravity. The support device can for example be in the form of a respective rotatable roller or possibly also in the form of a device which is not variable in position with respect to the holder of the support device, or can be constructed in some other suitable fashion, and can respectively bear against the upper and/or lower run.

The support device can at least partially project in height beyond the respective supporting run also on the side opposite to the C-shaped guide region of the guide apparatus and/or the facing side, in which respect attention is correspondingly directed to the description relating to the deflection device. In that way the line guide device is supported in a direction transversely to same by the support device by virtue of the projecting regions thereof when the line guide device, in the given displacement position of the guide apparatus is arranged beneath same in relation to the direction of the force of gravity, that is to say for example in the 6 o'clock position thereof.

The support device can be respectively arranged at the guide apparatus, in particular the C-arc thereof.

Preferably the line guide device is guided by the C-arc of the guide apparatus, wherein arranged on the side of the line guide device, that is opposite to the guide apparatus, is a holder for the guide apparatus on the machine or item of equipment. The holder preferably has a C-shaped holder portion. The guide apparatus is preferably displaceable in its longitudinal direction with respect to the holder. The line guide device can thus be arranged at least in some displacement positions over at least a part of its longitudinal extent, for example >25% or >50%, between the C-arc of the guide apparatus and the C-shaped holder portion. In that way on the one hand the line guide device is protected by the two oppositely disposed C-arcs, while on the other hand the C-shaped region of the holder, that extends in the longitudinal extent of the line guide device, can permit arcuate displacement of the guide apparatus, in which case said arcs are respectively preferably in the form of circular arcs.

Particularly preferably the holding region of the guide apparatus is displaceable in the longitudinal direction of the guide apparatus at the C-shaped holder portion in the longitudinal direction of the holder portion so that the guide apparatus on the one hand is displaceable with respect to the holder thereof, while on the other hand the holder region for the guide apparatus on the machine or item of equipment is also displaceable at the C-arc of the holder, whereby the possible overall displacement travel of the guide apparatus is increased in the longitudinal direction of the line guide device.

If the holder of the guide apparatus is in the form of a C-arc, more especially in the form of a portion of a circular arc, then the C-arc region of the holder extends over preferably >30° or >45° or >60°, possibly <90°.

The overall rotational angle of the C-arc of the guide apparatus, including a displacement of the guide apparatus with respect to the C-shaped holder thereof, is preferably >120° or >180° or >195° without the upper run and the lower run of one or two or more line guide devices arranged on the guide apparatus coming into contact with each other. That can apply in particular also when, in a displacement position of the guide apparatus, with the guide apparatus being displaced at a maximum with respect to the holder, a free end of the guide apparatus is disposed between the 12 o'clock position and the 4 o'clock position, for example in the 3 o'clock position, and the guide apparatus is displaced in the anti-clockwise direction, that is to say the line guide device in the displacement movement passes through the 12 o'clock position and is thus displaced overhead, that is to say through the 12 o'clock position.

Preferably the line guide device over the entire displacement travel thereof always bears with at least a region of one of its side boundaries against the guide apparatus, in particular the C-arc. Preferably the line guide device over the entire displacement travel thereof always bears with the entire longitudinal extent of the one of its side boundaries against the guide apparatus, in particular the C-arc thereof. Therefore, preferably over all the displacement positions of the line guide device, there is always only one and the same of the two side boundaries thereof bearing against the guide apparatus. That always gives a precise position for the line guide device, which also ensures better and more uniform displacement properties thereof. The fact of the line guide device always bearing against the guide apparatus can be ensured for example by suitable positioning of the deflection device at the line guide device.

Particularly preferably the C-shaped guide region of the guide apparatus or the guide apparatus overall is in the form of a portion of a circular arc. Upon a displacement of the guide apparatus in the longitudinal direction thereof therefore the end regions of the guide apparatus on said arcuate displacement and the envelope of the end regions of the displacement travel implemented or described by the guide apparatus will therefore lie on that circular arc. Accordingly the displacement travels of a device mounted at an end region of the guide apparatus or two devices mounted at the two opposite end regions of the guide apparatus are respectively also on a circular arc. That affords for example an optimum geometry in order to be able to detect or process an item or body to be investigated or processed, that is arranged on the curvature axis of the C-arc, for example a patient, from different spatial directions. In that way for example medical diagnostic in the examination of a patient can be improved. Optionally generally in accordance with the invention however the C-arc of the guide apparatus may also be of a non-circular arcuate configuration, for example it can be in the form of a portion of an ellipse or another arc shape.

Preferably the C-shaped guide region of the guide apparatus or particularly preferably the guide apparatus is arranged in relation to the guide region thereof for the line guide device over the entire displacement travel thereof, in one plane. Upon displacement of the guide apparatus and therewith also the C-arc thereof about the curvature axis of the guide apparatus the guide apparatus or the C-arc is thus moved in one plane. That is advantageous in particular when an object like for example a patient, arranged at the centre of the guide apparatus or on the curvature axis thereof, is to be examined by means of devices, with the at least one or more line guide devices, as is the case for example with a C-arc X-ray or MRI apparatus. The object or the person with the region which is to be examined or possibly also processed is then preferably arranged at the intersection of the C-arc with the curvature axis of the guide apparatus. For certain situations of use the C-arc of the guide apparatus however can also be of a different configuration and for example can also be in the form of part of a helix or spiral, in which case preferably the pitch of the helix or spiral is substantially less than the radius of the C-arc, for example being less than/equal to a fifth or less than/equal to a tenth.

Preferably the guide apparatus has a first and a second connecting device, wherein the first connecting device is connected to a first end region of the line guide device and the second connecting device is connected to the second end region of the line guide device. The first and second end region of the line guide device is preferably respectively connected to the respective connecting device in force-transmitting relationship. One of the two connecting devices, for example the first connecting device, is preferably stationarily connected to the guide apparatus or generally, upon displacement of the line guide device, is not connected variably in position in the longitudinal direction of the guide apparatus, but preferably permanently thereto. The other connecting device, for example the second connecting device, is preferably variable in position with respect to the guide apparatus, for example variable in position upon displacement of the line guide device with regard to same or with respect to the line guide device, in particular in relation to the longitudinal extent of the guide apparatus and/or the line guide device. At or in the region of the first and/or the second connecting device it is possible to provide a strain relief means for the line or lines like hoses, cables or the like, which are guided in the internal cross-section or the receiving space in the line guide device.

In a particularly preferred embodiment the guide apparatus, in addition to the first line guide device has (at least) a second line guide device, wherein both line guide devices, that is to say the first and the second, are respectively connected with a first end region at the first connecting device and both line guide devices are respectively connected with a second end region to the second connecting device, wherein the first line guide device, starting from the first connecting device, extends in a direction towards a first end region of the C-arc of the guide apparatus and the second line guide device, starting from the first connecting device, extends in a direction towards the second end region of the C-arc of the guide apparatus. The first and second line guide devices are thus arranged at the guide apparatus in mutually opposite relationship, that is to say in a loop-shaped configuration. Upon displacement of the guide apparatus in the direction of the longitudinal extent of the C-arc thereof therefore one of the two line guide devices, for example the first, is displaced in the direction towards its extended first position in which therefore the lower run of the line guide device is at a maximum length in relation to the displacement movement of the line guide device and the opposite run, that is to say the upper run, is at a minimum length. That displacement state of the first line guide device is referred to herein as displacement state lmax. In the displacement positions of the guide apparatus in which therefore the first line guide device is in the displacement state lmax, the displacement position is precisely reversed, that is to say the lower run of the second line guide device is in the displacement position lmax at a minimum length and the upper run is at a maximum length. The first and second line guide devices therefore substantially form a closed loop, wherein the two line guide devices respectively extend to another end or end region of the guide apparatus. In that case the first and second line guide devices are preferably guided by the same guide apparatus, in accordance with the respective displacement position of the two line guide devices a predetermined region of the guide apparatus can thus guide a portion of the first or the second line guide device, in particular in relation to the upper run thereof. The provision of a common guide apparatus for the first and second line guide devices has the advantage of a structurally particularly simple structure which in addition only occupies a small amount of space. Optionally—less preferred—it is however also possible to provide for the first and the second line guide devices, separate guide regions or separate guide apparatuses which for example in relation to the radial arrangement of the guide apparatus have a height-wise displacement relative to the curvature axis, that is to say are arranged at a different radial spacing relative to the curvature axis. Optionally the first and second guide apparatuses, for the first and second line guide devices respectively, can also involve a lateral displacement relative to each other, that is to say for example can be arranged at different portions of the curvature axis of the guide apparatus (specifically: the guide apparatus for the first line guide device), that is to say they can be arranged in succession in relation to the longitudinal direction of the curvature axis. Optionally it is also possible to provide more than two line guide devices at the guide apparatus.

The arrangement of a first and a second line guide device at the guide apparatus means that a larger number of lines like cables or hoses can be guided from the first connecting device to the second connecting device. That is for example advantageous if the receiving space in the first line guide device for lines is already occupied and it is necessary to guide further lines from the first to the second connecting device in order adequately to supply the technical device like for example a consumer at the end region of the guide apparatus with media which are carried in the lines.

In relation to the embodiment with two or more line guide devices, in relation to the features of the line guide devices and/or the guide apparatus and/or the machine or item of equipment, attention is generally directed to the other parts of description relating to the invention, possibly having regard to the respective differing directions in which the respective line guide device extends. That correspondingly also applies in relation to the parts of the description relating to the arrangement with only one line guide device insofar as that is not in conflict therewith or nothing different is involved in detail from the related context, having regard to the respective differing direction in which the respective line guide device extends. That also applies in relation to further devices described in the context of the invention like for example a support device or other devices.

For arrangements comprising only one line guide device, the description relating to the arrangement of two or more line guide devices correspondingly also applies insofar as it is not in conflict therewith.

Particularly preferably the two deflection devices of both line guide devices are positioned by a common device at the two deflection regions of the line guide devices and/or are subjected to a force in the longitudinal direction of the two line guide devices against the deflection regions thereof. Preferably in that case the deflection devices are in the form of deflection rollers. The common positioning device of the deflection devices ensures that the two deflection regions of the two line guide devices are preferably always arranged in their setpoint or target position, relative to the two line guide devices, over the entire displacement travel of the line guide devices. That avoids in particular unwanted changes in position of portions of the line guide devices, for example sagging of such portions which could adversely affect operational smoothness in the displacement movement of the line guide devices. In a structurally particularly simple fashion the axes of the deflection devices of the line guide devices, for example deflection rollers thereof, can be held at a predetermined spacing relative to each other by a spacer. The spacer can be rigid. In that way, the overall length of the arrangement of the two line guide devices is defined by the positions of the deflection devices, wherein each of the line guide devices, in the deflection region thereof, is guided around one of the deflection devices, bearing against same. If the two line guide devices are arranged in a loop-shaped configuration then a spacer for the deflection devices can also be arranged in the loop, in which case the spacer can be mounted in a floating relationship and can be entrained by the displacement of the line guide devices. The spacer can be rigid. In relation to the positioning of the deflection devices at the deflection regions of the line guide devices attention moreover is directed to the foregoing description, for example it is also possible to provide an actuator of positioning of the deflection devices, here too an actuator which couples to the deflection devices, applying a force jointly in different directions. The actuator for example can be arranged between the two deflection devices or deflection rollers and can exert thereon and/or on the bearings or holders, a spreading force in the direction of spacing the two deflection rollers from each other so that they hold the two deflection rollers at a constant spacing relative to each other and in that way position same at the two deflection regions of the two line guide devices and/or also apply force to the deflection devices in the longitudinal direction of the line guide devices, against the deflection regions.

Optionally a separate deflection device can also be provided for each of the deflection regions of the line guide devices. It is optionally also possible to provide a separate actuator for each of the two (or generally plurality of) deflection devices in order to position the respective deflection device at the deflection region of the respective line guide device.

Displacement of the deflection device for the respective deflection region in the arrangement of at least one or at least two line guide devices and positioning of the deflection device at the respective deflection region of the line guide device which is deflected around the deflection device can be implemented in differing ways. That applies in particular in relation to the arrangement of two line guide devices in a loop-shaped configuration, wherein the two deflection regions of the two line guide devices are oriented towards opposite end regions of the guide apparatus and are preferably arranged at a constant spacing in the longitudinal direction of the line guide devices. Preferred embodiments are described hereinafter.

In accordance with a first preferred embodiment U-I the at least one or the at least two deflection devices are positively guided by the line guide device deflected at same, that is to say the deflection device is necessarily altered in its position by the movement of the end region or regions of the at least one or preferably two end regions of two line guide devices arranged in a loop configuration. In the case of two line guide devices arranged in a loop configuration the two deflection devices arranged at the deflection regions can be held in their setpoint or target position by a spacer arranged in the loop, that is to say between the oppositely disposed deflection regions. The spacer can be at least substantially rigid, it can possibly also be elastically compressible under the application of a force in its longitudinal direction and can bear from the interior against the two opposite deflection regions, applying a force thereto. The spacer can be freely variable in position in relation to the guide apparatus in the longitudinal direction thereof. In that case the two end regions of the two line guide devices are preferably arranged at a connecting device or are fixed thereto in force-transmitting relationship. The connecting device can be fixed to the guide apparatus to carry the force and can thus act at an entrainment member or can be coupled in force-transmitting relationship to an entrainment member of the guide apparatus so that the end region or regions of the line guide device or devices and therewith also the deflection regions thereof are moved by the change in position of the entrainment member.

According to a further preferred embodiment U-II the at least one or the at least two deflection devices of the line guide device or devices are driven by motor means by means of a suitable drive in order to position the deflection device or devices at the deflection region or regions upon displacement of the line guide device. The motor drive preferably acts directly on the deflection device of the respective deflection region, with a variation in position thereof. The motor drive is preferably controlled electronically. Actuation of the motor drive can be implemented in dependence on a detected change in position of the guide apparatus so that the deflection region or regions are displaced by means of the drive synchronously with a change in position of the guide apparatus in the longitudinal direction of the line guide device. It will be appreciated that therefore there is a detection device for determining the position or change in position of the guide apparatus and a corresponding measurement value transmission to the control of the drive. Measurement value detection in respect of the position of the guide apparatus can be effected by detection of the actuation of the drive, like for example an electric motor of the guide apparatus. The end region or regions of the line guide device or devices can thus be connected to the guide apparatus floatingly or non-force-transmittingly. By way of example the drive can be held to the guide apparatus variably in position in the longitudinal direction thereof and can alter its position in the longitudinal direction of the guide apparatus by virtue of the drive force. The drive can also be mounted to another device of the machine or the item of equipment and can have an actuating element which is variable in position or length and which couples to the deflection device in order to position it appropriately, for example with a change in position with respect to the guide apparatus.

According to a further preferred embodiment U-III the setpoint or target position of the at least one or the at least two deflection devices of the line guide device or devices can be set in closed-loop readjustment fashion. For that purpose for example force pickup by sensor means can be effected at an entrainment member and/or fixed point of the line guide device or devices and/or a portion of the line guide device or devices and the deflection device at the respective deflection region of the line guide device is displaced by means of a suitable drive into its setpoint or target position with closed-loop readjustment, in which the force pickup is implemented in force-less fashion, that is to say it has a force action of zero and is thus adjusted in closed-loop control mode.

In a further preferred embodiment U-IV the at least one or the at least two deflection devices are positioned by means of a spring device in spring-prestressed condition in their setpoint or target position at the respective deflection region of the line guide device. The spring device for spring prestressing can be respectively coupled to the deflection device and can prestress same with respect to the respective deflection region or can be acted upon with a force by means of the spring, preferably in the line guide longitudinal direction. If the arrangement has a line guide device then the support abutment of the spring prestressing device can be arranged for example at the guide apparatus or the C-arc thereof, preferably arranged stationarily in relation thereto. If there are two line guide devices which are arranged in a loop configuration and which therefore extend to opposite ends of the C-arc of the guide apparatus then there can be provided a spring stressing device which engages both opposite deflection regions or the deflection devices thereof and with a spring force holds same in the setpoint or target position thereof or acts thereupon with a force in the spacing direction thereof. It is also possible to provide in relation to each of the deflection regions separate spring prestressing devices which for example each have a support abutment on the guide apparatus or the C-arc thereof.

The invention further includes a machine or an item of equipment, in particular a C-arm X-ray or C-arm MRI unit, comprising a guide apparatus according to the present invention, including the line guide device. In general the respective machine or item of equipment can be a medical device like diagnostic devices or however can also be a machine or a device for material processing or working without being respectively limited thereto.

Preferably the machine or the item of equipment has a holder for the guide apparatus, the guide apparatus being displaceable in its longitudinal direction with respect to the holder. Generally in accordance with the invention the at least one, two or possibly also more of line guide device or devices guided by the guide apparatus is/are also surrounded, on the side opposite to the C-arc of the guide apparatus, by a C-shaped component so that the one, two or possibly more line guide devices is or are surrounded on two opposite sides by C-arcuately shaped components. The C-shaped component which is opposite to the C-arc of the guide apparatus in relation to the line guide device or devices, in particular in the configuration in the form of a C-arc, preferably represents the holder for the guide apparatus on the machine or item of equipment or a part of the holder or is connected thereto or represents a part of a housing which encloses the line guide device or devices, wherein generally the housing can be completely closed or however can also be partially open. With displacement of the guide apparatus with respect to the C-shaped component like for example a holder part therefore a telescopic movement can be performed, more precisely a telescopic movement involving an arcuate configuration. The C-arc of the guide apparatus and the arcuate holder region or C-arc of the holder, in the sense of a holder for the guide apparatus, can in that case be in the form of concentric arcs, in particular concentric circular arcs.

The C-shaped component which is opposite to the guide apparatus preferably extends over >15% or >25% or possibly even >50% over the longitudinal extent of the line guide device or devices, this being intended to mean the respective maximum length of the line guide device or devices in the completely extended state thereof.

Generally in accordance with the invention the guide apparatus, in particular the C-arc thereof, can be arranged on a carriage, the guide apparatus being arranged displaceably in its longitudinal direction with respect to the carriage. The guide apparatus can be fixed in that case to the carriage. The carriage in turn can be arranged on the holder of the machine or item of equipment for the guide apparatus, wherein the carriage can be displaceable relative to the holder in the longitudinal direction thereof or in the longitudinal direction of the guide apparatus. The arrangement of the carriage provides that between the C-arc of the guide apparatus and the holder there is a spacing in which preferably the line guide device or devices is or are arranged. In addition that arrangement can provide that a consumer arranged at the guide apparatus or a technical device which is supplied with media by the line or lines arranged in the line guide device or devices can be displaced over a greater arcuate region, possibly over the total length of both C-arcs, and that expands the area of use of the machine or item of equipment.

Generally in accordance with the invention the axis of the C-arc of the guide apparatus is preferably arranged transversely or perpendicularly to the direction of the force of gravity, that is to say to the Z-axis of the installation area of the machine or item of equipment including the guide apparatus. The axis (that is to say curvature axis) of the C-arc can preferably involve an angle of 30 to 150°, preferably 45° to 135°, particularly preferably 60° to 120° or about 90° relative to the direction of the force of gravity. With this arrangement the advantages of the guide apparatus according to the invention are particularly important.

The connecting device for the two first end regions of the two line guide devices (or possibly also for more than two line guide devices) preferably forms a fixed point in relation to the displacement of the line guide device or devices and is mounted to the holder for the guide apparatus preferably in non-longitudinally displaceable relationship or particularly preferably stationarily. The two or more end regions of the line guide devices can in that case be fixed to a common component, but possibly also to a plurality of components which are preferably not variable in position relative to each other. The connecting elements of the connecting device which respectively directly fix or hold an end region of the respective line guide device can be arranged spaced from each other, in which case that spacing preferably does not change upon displacement of the guide apparatus and therewith also the line guide devices. The two connecting elements can be arranged on one and the same component of the holder or generally of the machine or item of equipment like for example a flange or collar or also on various components of the machine or item of equipment. A corresponding consideration can apply independently thereof or in combination therewith for the two connecting elements of the other (second) connecting device which for example can be arranged at an entrainment member of the line guide devices for displacement thereof.

BRIEF DESCRIPTION OF THE DRAWINGS

The invention will be described by way of example hereinafter and by means of embodiments and with reference to the Figures. All features of the embodiments by way of example are deemed to be disclosed independently of each other in the general context of the invention. Identical components are denoted in the various Figures by the same references. In the drawings.

DETAILED DESCRIPTION

The machine or item of equipment 1 according to the invention, here by way of example in the form of a C-arm X-ray device or a C-arm MRI device, includes a guide apparatus 1 for a line guide device with at least one such line guide device 10 (see FIGS. 1-5). The line guide device 10 has a continuous free internal cross-section 11 extending in the longitudinal direction thereof for receiving at least one line 12 like a hose, cable or the like. The line guide device 10 has a plurality of portions 13 which are arranged in succession in the longitudinal direction thereof and which can be spatially deflected relative to each other. The line guide device 10 is disposed in an arrangement comprising a lower run 14, an upper run 15 and a deflection region 16 connecting them, wherein the deflection region 16 has a deflection axis 16a, about which the line guide device 10 is deflected. The line guide device 10 has two side boundaries 17a, 17b, the lateral spacing of which relative to each other determines the width of the line guide device 10 and wherein the side boundaries are arranged at least substantially perpendicularly to the mutually facing upper and lower sides 15a, 14a of the upper and lower runs 15, 14. The guide apparatus 5 is formed at least with a longitudinal portion thereof or over its entire length, with which it guides the line guide device 10 in the longitudinal direction thereof, with a C-shaped guide region 6 having a curvature axis 6a of the C-arc and with a concave arc internal curvature 6c and a convex arc external curvature 6d.

Provided at an end region of the guide apparatus 5 is a holder 76 for fixing a technical device 75 like for example a consumer which is supplied with the lines guided by the line guide device or devices 10, 100, wherein the lines are fed from the machine or item of equipment from the connecting point 1a.

According to the subject of the invention and as shown in FIGS. 1-5 the guide apparatus 5 has a deflection device 20 having a deflection axis 20a, wherein the deflection region 16 of the line guide device 10 is guided around the deflection device 20. The axis 20a of the deflection device 20 includes an angle with the curvature axis 6a of the C-shaped guide region 6 of the guide apparatus 5, here an angle of 90°. The angle of the deflection axis 20a of the deflection device 20 for the line guide device 10 relative to the curvature axis 6a of the C-shaped guide region of the guide apparatus is here 90°. In this case the curvature axis 6a corresponds to the axis of rotation, about which the guide apparatus is rotatable.

One of the side boundaries 17a of the line guide device 10 is arranged facing the convexly curved outside 6d of the C-shaped guide region 6 of the guide apparatus 5. The side boundary 17a (and preferably only that one side boundary) of the line guide device 10 bears in the displacement of the line guide device over at least a part of the longitudinal extent thereof against the convexly curved outside of the C-shaped guide region of the guide apparatus, here over the entire displacement travel or the entire displacement of the line guide device between its two end points of the displacement travel, that is to say the maximum displacement in the one displacement direction and the other. In this case the line guide device can laterally bear against the C-arc of the guide apparatus over >50% or >75% or >90%, preferably at least approximately, for example as far as the region of the line guide device at the deflection device, practically over the entire length thereof. In this arrangement the guide apparatus bears only against the side boundary of the line guide device, that is to say not for example against the top side of the upper run or the underside of the lower run, which reduces friction and structural complication, which however can possibly also be the case.

The described structure means that the guide apparatus 5 with the line guide device 10 is of an only small structural height, that is to say a short radial extent in relation to the curvature axis of the C-arc of the guide or the axis of rotation of the guide apparatus. In that way the guide can be further displaced in the direction of the installation surface A of the machine or item of equipment or the installation surface does not impede displacement of the guide apparatus with line guide device towards the installation surface and beyond, that is to say beyond the 6 o'clock position U6 in the direction towards the 3 o'clock position U3. In addition this prevents the upper run from hanging down when the line guide device is "upside down", that is to say in the 12 o'clock position U12, so that it cannot come into contact with the lower run, as can conventionally be the case, as the line guide device is laid "on the side", that is to say supported laterally at the guide apparatus.

The C-shaped guide region 6 of the guide apparatus 5 extends here over >50%, more precisely 100%, of the longitudinal extent of the line guide device 10 in the displacement state thereof at the maximum spacing of the two end regions 10a, 10b of the line guide device 10 relative to each other in both displacement directions of the line guide device.

Provided here is a device 25 for changing the position of the deflection device 20 in the longitudinal direction of the line guide device 10, which positions the deflection device 20 in its position at the deflection region 16 of the line guide device 10 independently of the displacement position of the line guide device 10. That is achieved here in that the deflection device 20 is arranged and fixed to the guide apparatus and the guide apparatus thus positions the deflection device 20 at the deflection region 16. For setting the positioning the deflection device is displaceable with respect to the guide apparatus in the longitudinal direction thereof, for example manually, and can be fixed in its setpoint or target position with respect to the guide apparatus, more precisely at same. Positioning of the deflection device 20 can however also be effected in another way, thus in an alternative embodiment for example the deflection device can be positioned by an actuator at the deflection region, in which case the actuator is actuated for example in dependence on the displacement position of the guide apparatus and/or of the line guide device.

The deflection device 20 is mounted displaceably by means of a bearing 21. The bearing 21 is here held longitudinally displaceably to the C-shaped guide region of the guide apparatus. The deflection device 20 is here in the form of a rotatable deflection roller.

The deflection device 20 here projects beyond the line guide device 10 over a part of the height thereof in relation to the upper run and the lower run, in the illustrated embodiment by about 25% of the height thereof respectively, for which purpose the deflection device in the form of the deflection roller has a channel-shaped radial outside surface about which the line guide device is deflected so that the line guide device is therefore arranged in the channel.

A support device 28 is further provided for the upper and/or lower run of the line guide device, for supporting the upper and/or lower run outside the deflection region in the direction towards the respective other run. In this arrangement the support device bears against both the upper and lower run, possibly also only against the upper run or the lower run, in which case a separate support device can be provided for the respective other run. The support device is here in the form of a rotatable support roller. The support device projects beyond the respective run against which the support device bears in respect of height, for example by about 20% on the side opposite the C-arc of the guide apparatus or here on both sides. In that way the target position of the line guide device is additionally stabilised, with the arrangement of the axis of rotation of the C-arc of the guide apparatus being perpendicular to the direction of the force of gravity, but in particular also in an inclined position relative to same, that is to say at a non-perpendicular angle. The support roller can be designed like the deflection roller.

The line guide device 10 always bears over the entire displacement travel thereof with at least a region of one of its side boundaries 17a against the guide apparatus 5, here practically over the entire longitudinal extent of the side boundary.

The C-shaped guide region 6 of the guide apparatus 5 is in the form of a circular arc. The C-arcuate guide region 6 of the guide apparatus is arranged in one plane.

The guide apparatus 5 has a first connecting device 30 and a second connecting device 35, wherein the first connecting device 30 is connected to a first end of the line guide device 10 and the second connecting device 35 is connected to the second end of the line guide device 10. In this arrangement the first connecting device 30 is variable in position with respect to the guide apparatus 5 and thus also with respect to the C-shaped guide region 6 thereof and for example is arranged on or fixed to the holder of the machine or item of equipment for the guide apparatus, wherein the guide apparatus is displaceable with respect to the holder. In this arrangement the first connecting device 30 forms a fixed point in relation to the displacement of the line guide device. The second connecting device 35 is arranged stationarily with respect to the guide apparatus 5 and the C-arc thereof, more precisely it is fixed to the guide apparatus 5. The second connecting device 35 thus represents an entrainment member for the line guide device 10 upon displacement thereof.

It will be appreciated that the guided line or lines are suitably guided from the first connecting device 30 to the connecting point 1a of the machine or item of equipment, this is not shown in the Figures.

The guide apparatus 5 has here, in addition to the first line guide device 10, a second line guide device 100, wherein both line guide devices 10, 100 are respectively connected with a first end to the first connecting device 30 and both line guide devices 10, 100 are respectively connected with a second end thereof to the second connecting device 35. The first line guide device 10 extends from the first connecting device 30 in the direction towards a first end of the C-shaped guide region 6 of the guide apparatus 5. The second line guide device 100 extends from the first connecting device 30 in the direction towards the second end of the C-shaped guide region 6 of the guide apparatus 5. The said first and second ends represent the ends of the guide apparatus, which are in opposite relationship in the longitudinal direction thereof. The two line guide devices 10, 100 are thus arranged in a loop formation.

The description relating to the first line guide device 10 correspondingly also applies here for the second line guide device 100, including the descriptive statements relating to the deflection device, having regard to the different directions in which the two line guide devices 10, 100 extend.

One or here both of the connecting devices 30, 35 have separate connecting elements for the two line guide devices 10, 100, wherein the two connecting elements can be arranged adjacent to each other at the respective connecting device. Provided at the connecting elements or in the region thereof is a respective strain relief means for lines which are guided by the line guide device connected to the respective connecting element.

The two deflection devices 20, 120 of the two line guide devices 10, 100 are positioned by a common device at the two deflection regions 16, 116 of the line guide devices 10, 100. The common device is the guide apparatus, more precisely the C-arc thereof. The two deflection devices 20, 120 are subjected to a force in the longitudinal direction of the two line guide devices 10, 100 against the respective deflection region, for which purpose in the simplest case the deflection device is positioned upon fitment thereof in such a way as to exert a force at the deflection regions and then fixed in that position for example at the guide apparatus.

FIGS. 4A-4D show diagrammatic views of various configurations U-I to U-IV in relation to the positioning of the deflection device or devices in the target position thereof at the respective deflection region of the line guide device or devices (FIGS. 4A-4D). The embodiments are respectively illustrated with a guide apparatus 5 having two line guide devices 10 arranged in a loop configuration, it will be appreciated that corresponding embodiments can also be implemented as guide apparatuses with only one line guide device.

In a first embodiment U-I (FIG. 4A) the two deflection devices 420 are positively guided by the line guide device 410 deflected at same and are forcibly changed in their position by the displacement of the end regions of the two ends, which are brought together at a moveable connecting device, of the two line guide devices which are arranged in a loop configuration. The two deflection devices are arranged in the loop of the two line guide devices. The two deflection devices are held in their target or setpoint position relative to each other by a rigid spacer 415 and thus upon displacement of the line guide devices are arranged in their respective target position at the deflection regions. Upon displacement of the line guide devices in one direction therefore the spacer moves with the line guide devices.

In an embodiment U-II (FIG. 4B) the two deflection devices 420 of the line guide device or devices 410 are driven by motor means by means of a suitable drive 430 in order to position the deflection device or devices at the deflection region or regions upon displacement of the line guide device. The motor drive 430 acts directly on the deflection device 420 with the deflection axis 420a of the respective deflection region, with a change in position. The motor drive is controlled electronically by means of the control arrangement 432, in dependence on a detected change in position of the guide apparatus, here with detection of the operating parameters of the drive of the guide apparatus. Associated with each of the deflection devices 420 is a separate drive 430 for the change in position thereof, a common drive can possibly also be provided by virtue of a suitable coupling mechanism. The drive here is held variably in position at the guide apparatus 5.

In the embodiment U-III (FIG. 4C) the target position of the deflection devices 420 is set in closed-loop re-adjustment mode at the deflection regions 416 of the line guide devices 410. For that purpose there is provided a sensor force pickup 437 at an entrainment member 438 and/or fixed point of at least one or both of the line guide devices and/or a portion of at least one or both of the line guide devices. The deflection device 420 at the respective deflection region 416 of the line guide device 410 is displaced by means of a suitable drive 440 into its target position, with closed-loop re-adjustment thereof. A common drive can be provided for the two deflection devices, or separate drives can be provided for that purpose, which are respectively actuated in closed-loop adjustment mode. In that arrangement a connecting device for the end region or regions of the one or both line guide devices can be provided, which is not coupled to the guide apparatus, which generally can be the case in accordance with the invention.

In the embodiment U-IV (FIG. 4D) the at least one or the at least two deflection devices 420 with deflection axis 420*a* are positioned in a spring-prestressed condition by means of a spring device 450 in their target position at the respective deflection region 416 of the line guide device 410. The spring device for spring prestressing can respectively couple to the deflection device and can prestress same with respect to the respective deflection region or can subject same to a force by means of the spring action, preferably in the line guide longitudinal direction. Depending on the respective arrangement of the support abutment for the spring device and the direction of displacement of the line guide device the spring element can be in the form of a tension spring or a compression spring. If there are two line guide devices 410 arranged in a loop configuration then a spring stressing device can engage both oppositely disposed deflection regions 416 and hold same in their target position, or can act upon them with a spring force away from each other in the spacing direction of the deflection regions.

The machine or item of equipment 1 (FIGS. 5A-5B) has a holder 50 for the guide apparatus, the guide apparatus 5 being displaceable in the longitudinal direction thereof with respect to the holder 50. Provided on the side of the line guide device 10, that is opposite to the guide apparatus, is a C-shaped portion 51 which in the embodiment is also fixed to the holder 50 and which here is in the form of a portion of a circular arc. The two C-arcs 6, 51 are arranged concentrically relative to each other about the curvature axis 6*a*.

Figure 5A:
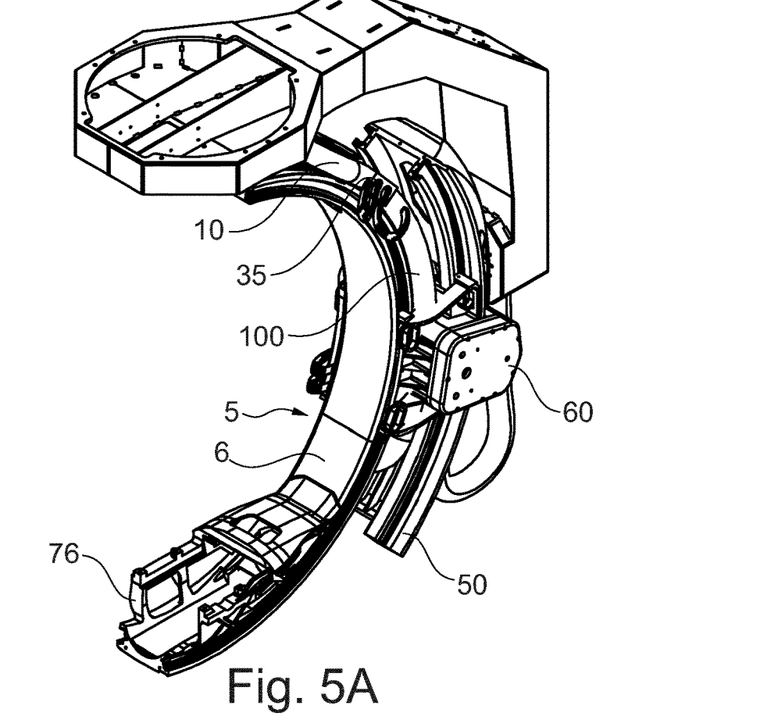
FIGS. 5A-5B show a part of a machine or item of equipment with a guide apparatus according to the invention and line guide devices according to a first assembly (FIG. 5A) and a second assembly (FIG. 5B).
Figure 5B:
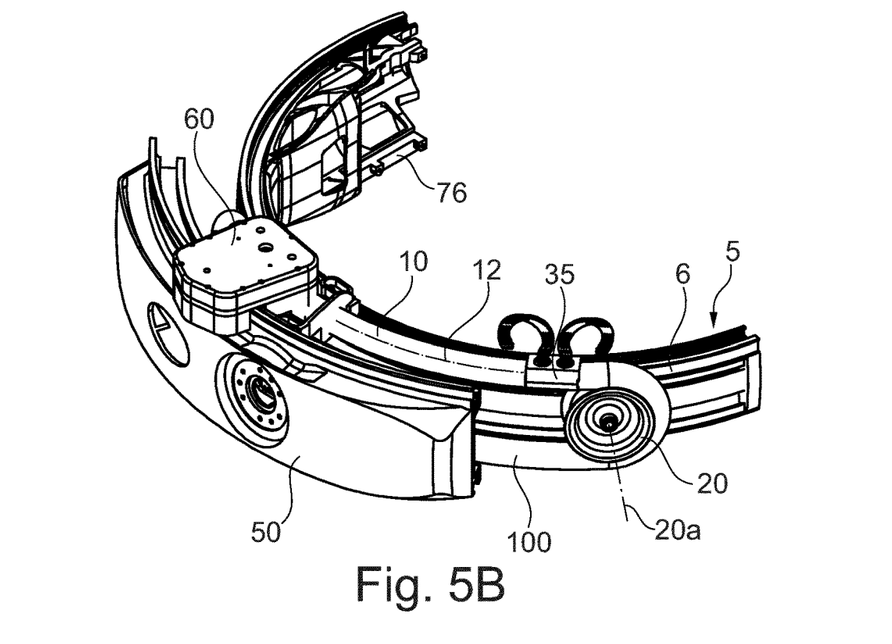

The guide apparatus 5 is here mounted to a carriage 60 and is displaceable with respect thereto in the longitudinal direction of the apparatus 5. The carriage 60 is in turn mounted to the holder 50, more specifically at the C-arc thereof, and also displaceable at the C-arc of the holder 50 in its longitudinal direction. The guide apparatus 5 and the holder 50 are thus spaced from each other in the radial direction and the line guide device or devices 10, 100 are arranged in that spacing region.

Figure 1A:
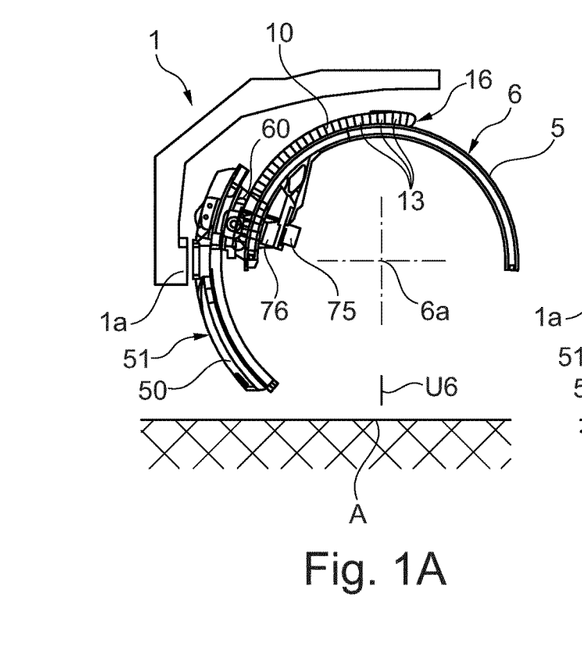
FIGS. 1A-1C show diagrammatic views of a guide apparatus according to the invention with line guide devices in a first displacement position (FIG. 1A), a second displacement position (FIG. 1B) and a third displacement position (FIG. 1C)

The C-arc 6 of the guide apparatus extends over about 180°. The C-arc of the holder extends through about 90°. As shown in FIGS. 1A and 1C the end region of the guide apparatus 5, at which there is disposed a technical device 75 supplied with the guided lines, is thus freely displaceable through about 280°, the guide apparatus with line guide device being particularly suitable for that.

The guide apparatus 5 is mounted to the machine or item of equipment 1 in such a way that the curvature axis 6*a* of the C-shaped guide region 6 is arranged at an angle relative to the direction of the force of gravity, here at an angle of 90°. The direction of the force of gravity is thus in the main axis of the C-arc 6 of the guide apparatus. The guide apparatus is here pivotable, with a change in the angle of the curvature axis or axis of rotation relative to the direction of the force of gravity, wherein in the illustrated embodiment the pivot axis extends through the centre of the holding region of the holder 50 for the guide apparatus. The holder 50 with the C-arc 51 is held pivotably to the machine or the item of equipment together with the guide apparatus 5 and therewith also the line guide device or devices 10, 100 arranged thereon. The spatial position of the line guide device or devices 10, 100 also changes by virtue of that pivotal movement, wherein the configuration according to the invention of the guide apparatus stabilises the line guide device or devices in an exact position in a particularly suitable fashion in the different spatial arrangements and ensures good operating properties of the line guide device with a low level of wear.

Figure 1B:
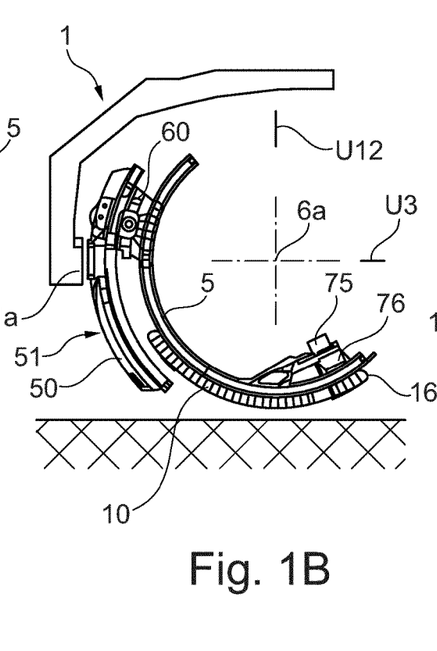
Figure 1C:
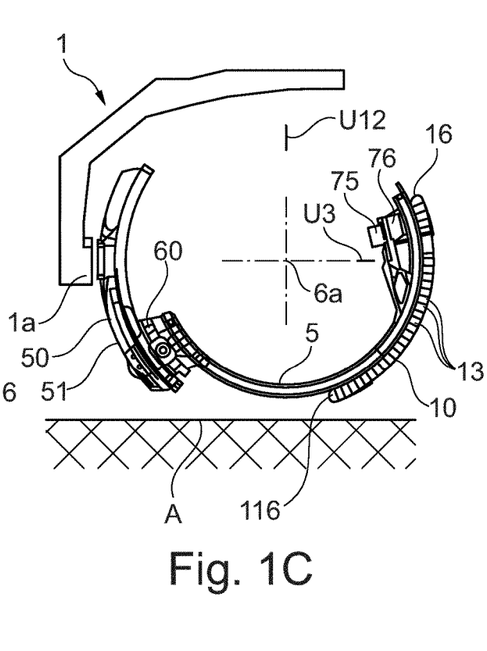
Figure 2A:
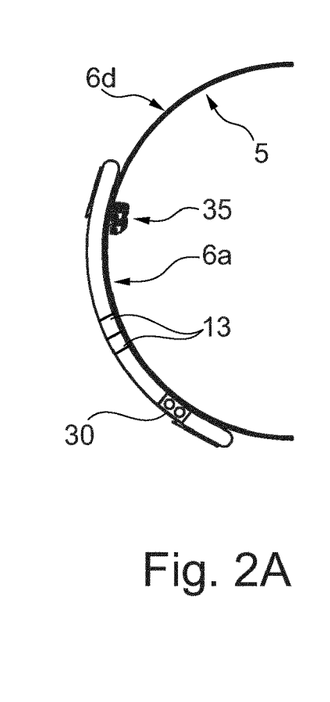
FIGS. 2A-2C show diagrammatic views of a guide apparatus according to the invention with two line guide devices in a side view (FIG. 2A), a plan view (FIG. 2B) and a perspective view (FIG. 2C)
Figure 2B:
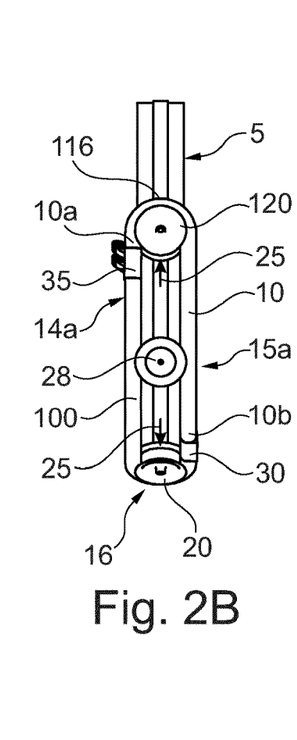
Figure 2C:
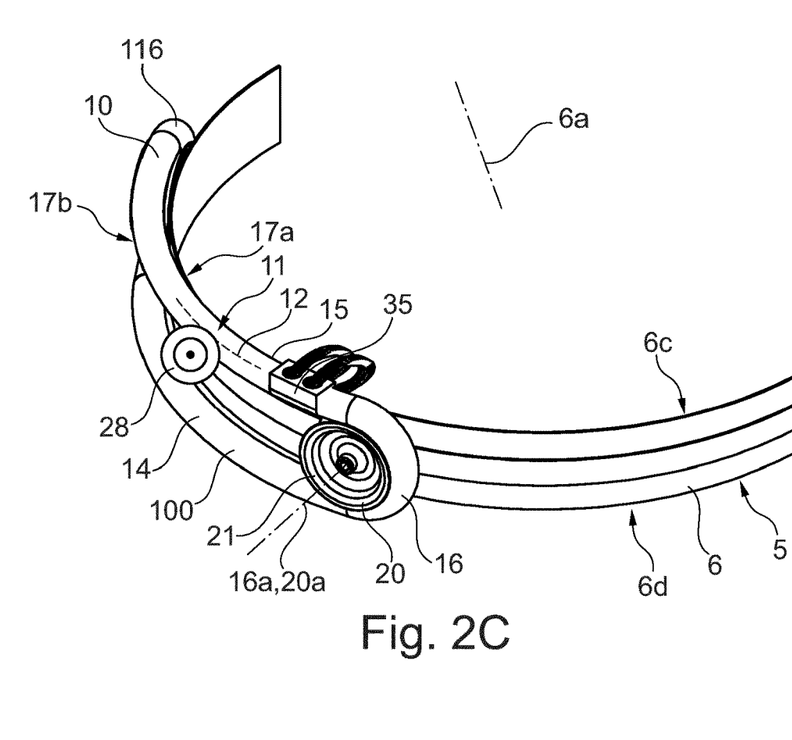
Figure 3A:
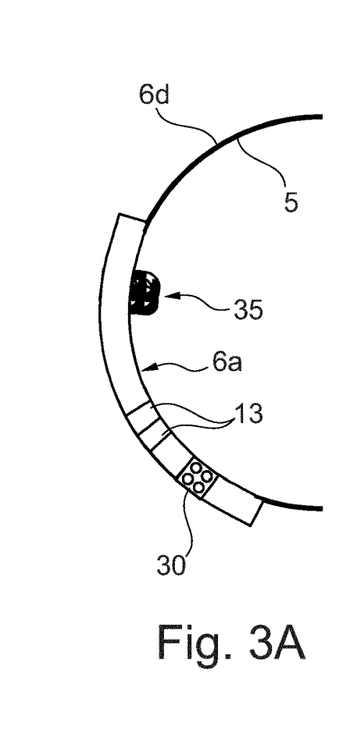
FIGS. 3A-3C show diagrammatic views of a further embodiment of a guide apparatus according to the invention with two line guide devices in a side view (FIG. 3A), a plan view (FIG. 3B) and a perspective view (FIG. 3C)
Figure 3B:
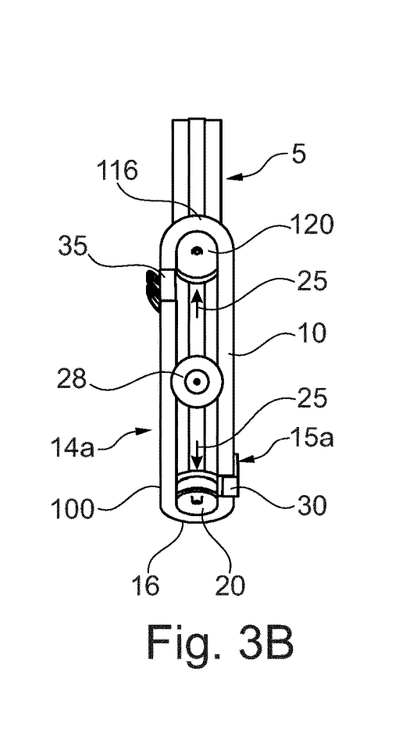
Figure 3C:
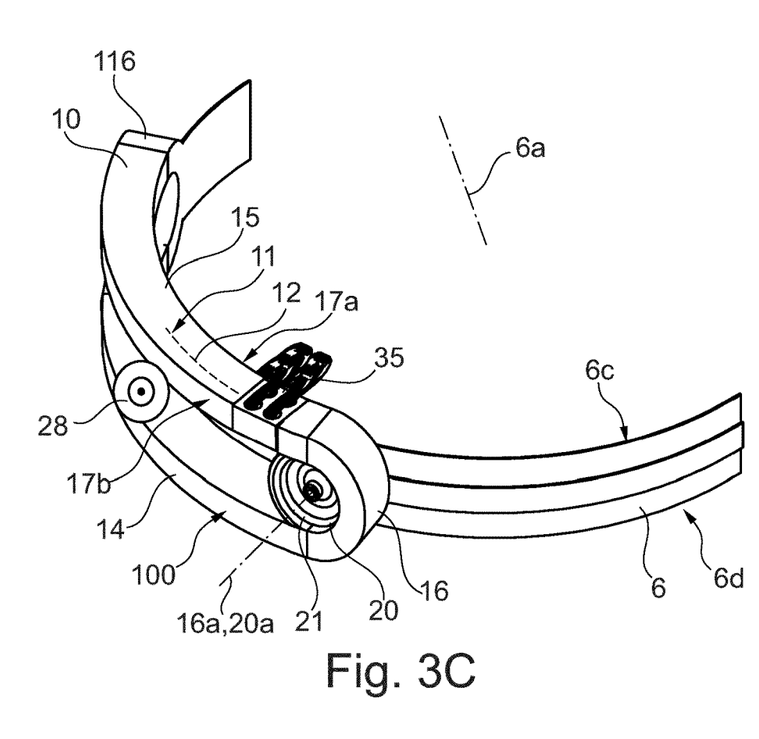
Figure 4A:
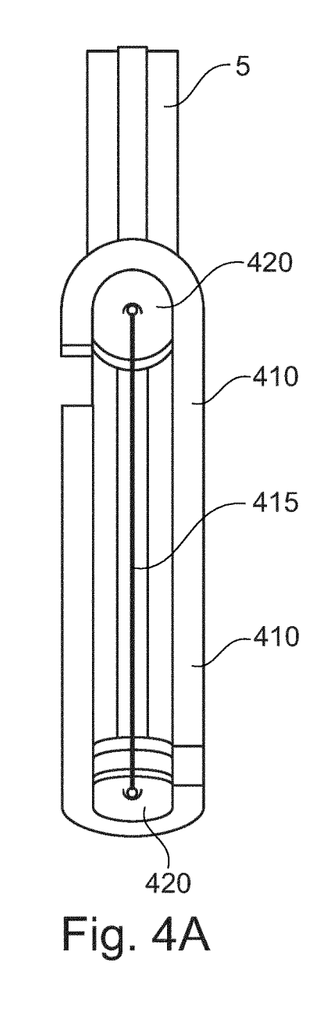
FIGS. 4A-4D show diagrammatic views of various embodiments U-I to U-IV relating to setting of the deflection device or devices in the target position thereof at the respective deflection region of the line guide device or devices (FIGS. 4A-4D)
Figure 4B:
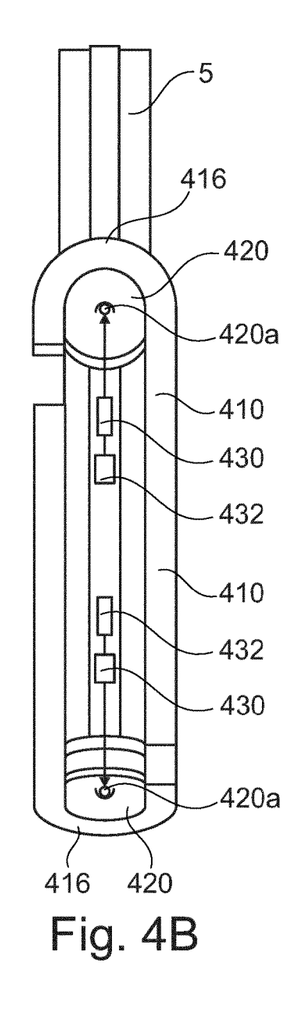
Figure 4C:
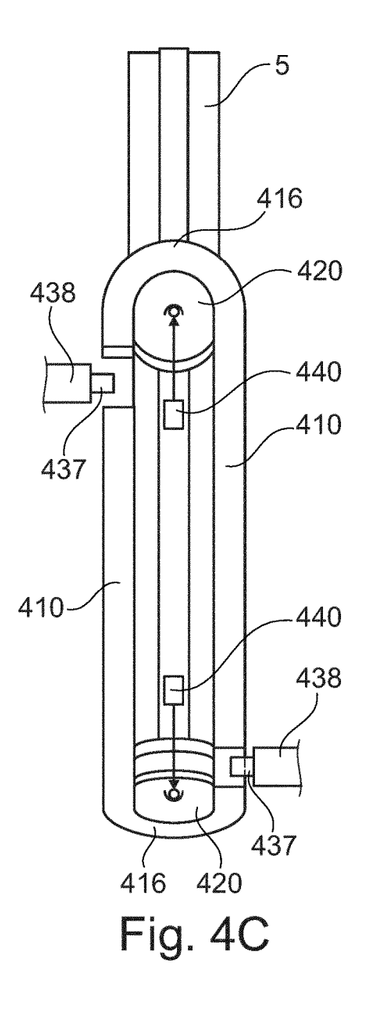
Figure 4D:
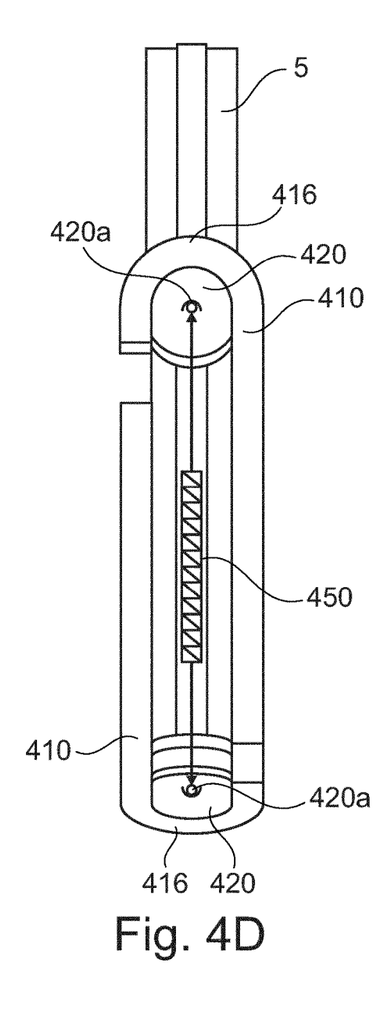

In addition and possibly independently thereof or in combination therewith the holder 50 holding the guide apparatus can be tilted together with the guide apparatus 5 in a plane which is tilted relative to the plane of the arrangement of the guide apparatus as shown in FIGS. 1A-1C (that is to say the plane of the paper in the Figures) so that accordingly in relation to the main plane of the guide apparatus, as shown in FIGS. 1A-1C, it is tilted out of or into the main plane.

What is claimed is:

1. A guide apparatus for a line guide device comprising at least one such line guide device, wherein the line guide device has a continuous free internal cross-section extending in the longitudinal direction thereof for receiving at least one line like a hose, cable or the like, and wherein the line guide device has a plurality of portions which are arranged in succession in the longitudinal direction thereof and which are spatially deflectable relative to each other and the line guide device is disposed in an arrangement comprising a lower run, an upper run and a displaceable deflection region connecting same, wherein the deflection region has a deflection axis, about which a line guide device is deflected, and wherein the line guide device has two side boundaries, the lateral spacing of which relative to each other determines the width of the line guide device and wherein the side boundaries are arranged substantially perpendicularly to the mutually facing upper and lower sides of the upper and lower run and wherein the guide apparatus is formed at least with a longitudinal portion thereof or over its entire length, with which it guides the line guide device in the longitudinal direction thereof, with a C-shaped guide region with a curvature axis of the C-arc and with a concave arc internal curvature and a convex arc external curvature, wherein the guide apparatus has a deflection device having a deflection axis and the deflection region of the line guide device is guided around the deflection device, the axis of the deflection device includes an angle with the curvature axis of the C-shaped guide region of the guide apparatus and one of the side boundaries of the line guide device is arranged facing towards the convexly curved outside of the C-shaped guide region of the guide apparatus.

2. The guide apparatus according to claim 1, wherein the angle of the deflection axis of the deflection device for the line guide device relative to the curvature axis of the C-shaped guide region of the guide apparatus is 45° to 135°, preferably about 90°.

3. The guide apparatus according to claim 1, wherein the C-shaped guide region of the guide apparatus extends over at least 50% or 100% of the longitudinal extent of the line guide device in the displacement state thereof with the maximum spacing of the two end regions of the line guide device relative to each other.

4. The guide apparatus according to claim 1, wherein there is provided a device for changing the position of the deflection device in the longitudinal direction of the line guide device, which positions the deflection device in its position at the deflection region of the line guide device independently of the displacement position of the line guide device.

5. The guide apparatus according to claim 4, wherein the deflection device is mounted rotatably by means of a bearing and that the bearing is held longitudinally displaceably at the C-shaped guide region of the guide apparatus.

6. The guide apparatus according to claim 1, wherein the deflection device is in the form of a rotatable deflection roller.

7. The guide apparatus according to claim 1, wherein the line guide device always bears over the entire displacement travel thereof with at least one region of one of its side boundaries against the guide apparatus.

8. The guide apparatus according to claim 1, wherein the C-shaped arc of the guide region of the guide apparatus is in the form of a circular arc.

9. The guide apparatus according to claim 1, wherein the C-shaped guide region of the guide apparatus is arranged in one plane.

10. The guide apparatus according to claim 1, wherein the guide apparatus has a first connecting device and a second connecting device, wherein the first connecting device is connected to a first end of the line guide device and the second connecting device is connected to the second end of the line guide device.

11. The guide apparatus according to claim 10, wherein the first connecting device is arranged variably in position with respect to the C-shaped guide region of the guide apparatus and the second connecting device is arranged stationarily with respect to the C-shaped guide region of the guide apparatus.

12. The guide apparatus according to claim 10, wherein the guide apparatus has a second line guide device in addition to the first line guide device, wherein both line guide devices are respectively connected with a first end at the first connecting device and both line guide devices are respectively connected with a second end thereof to the second connecting device and that the first line guide device starting from the first connecting device extends in the direction towards a first end of the C-shaped guide region of the guide apparatus and the second line guide device starting from the first connecting device extends in the direction towards the second end of the C-shaped guide region of the guide apparatus.

13. The guide apparatus according to claim 12, wherein the two deflection devices of the two line guide devices are positioned by a common device at the two deflection regions of the line guide devices and/or are subjected to a force in the longitudinal direction of the two line guide devices against the respective deflection region of the line guide device.

14. The guide apparatus according to claim 1, wherein the guide apparatus is mounted to a C-shaped holder and the guide apparatus is displaceable along the direction of the C-arc of the holder.

15. The guide apparatus according to claim 1, wherein the line guide device is guided bearing loosely against the deflection device around same.

16. An item of equipment or machine comprising a guide apparatus according to claim 1.

17. The item of equipment or machine according to claim 16, wherein the item of equipment or the machine has a holder for the guide apparatus and the guide apparatus is displaceable in the longitudinal direction thereof with respect to the holder.

18. The item of equipment or machine according to claim 16, wherein the guide apparatus is mounted to the item of equipment or the machine in such a way that the curvature axis of the C-shaped guide region is arranged at an angle relative to the direction of the force of gravity, preferably an angle of 90°.

19. The item of equipment according to claim 16, wherein the item of equipment is in the form of a C-arm X-ray device or a C-arm MRI device.

* * * * *